United States Patent
LaBelle et al.

(10) Patent No.: US 11,185,263 B2
(45) Date of Patent: Nov. 30, 2021

(54) BIOSENSOR ARRAY FOR THE DETECTION OF ANALYTES

(71) Applicants: Jeffrey LaBelle, Tempe, AZ (US); David Probst, Tempe, AZ (US); Bin Mu, Tempe, AZ (US)

(72) Inventors: Jeffrey LaBelle, Tempe, AZ (US); David Probst, Tempe, AZ (US); Bin Mu, Tempe, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 298 days.

(21) Appl. No.: 16/198,363

(22) Filed: Nov. 21, 2018

(65) Prior Publication Data
US 2019/0150815 A1 May 23, 2019

Related U.S. Application Data

(60) Provisional application No. 62/589,066, filed on Nov. 21, 2017.

(51) Int. Cl.
*A61B 5/1486* (2006.01)
*A61B 5/145* (2006.01)
(Continued)

(52) U.S. Cl.
CPC ...... *A61B 5/14865* (2013.01); *A61B 5/14546* (2013.01); *A61B 5/14735* (2013.01);
(Continued)

(58) Field of Classification Search
CPC ........... G01N 2333/62; G01N 27/3275; G01N 27/3271; C12Q 1/006; A61B 5/14865;
(Continued)

(56) References Cited

U.S. PATENT DOCUMENTS

| 7,869,853 B1* | 1/2011 | Say | A61B 5/14532 600/347 |
| 2006/0076236 A1* | 4/2006 | Shah | C12Q 1/006 204/403.01 |

(Continued)

FOREIGN PATENT DOCUMENTS

| WO | 2012009322 A1 | 1/2012 |
| WO | 2016025153 A1 | 2/2016 |
| WO | 2018175448 A1 | 9/2018 |

OTHER PUBLICATIONS

Natural and Biomimetic Materials for the Detection of Insulin Romana Schirhagl, Usman Latif, Dagmar Podlipna, Hans Blumenstock, and Franz L. Dickert Analytical Chemistry 2012 84 (9), 3908-3913 DOI: 10.1021/ac201687b.*

(Continued)

*Primary Examiner* — Sean P Dougherty
*Assistant Examiner* — Kyle W. Kretzer
(74) *Attorney, Agent, or Firm* — Michael Best & Friedrich LLP

(57) ABSTRACT

Embodiments of the present disclosure relate generally devices for detecting analytes in a subject. More particularly, the present disclosure provides a biosensor array for detecting analytes in a subject. Embodiments of the present disclosure include a biosensor array comprising a plurality of sensor cells for detecting an analyte in a subject. In accordance with these embodiments, the plurality of sensor cells comprise at least one electrode, at least one antibody immobilized on a surface of the at least one electrode, and a biodegradable coating in contact with the at least one antibody.

6 Claims, 15 Drawing Sheets

(51) Int. Cl.
*A61B 5/1473* (2006.01)
*G01N 27/327* (2006.01)

(52) U.S. Cl.
CPC ............. *A61B 5/145* (2013.01); *A61B 5/1486* (2013.01); *A61B 5/14503* (2013.01); *A61B 5/14507* (2013.01); *G01N 27/3271* (2013.01); *G01N 27/3275* (2013.01); *G01N 2333/62* (2013.01)

(58) Field of Classification Search
CPC . A61B 5/14735; A61B 5/14546; A61B 5/145; A61B 5/14507; A61B 5/1486; A61B 5/14503
See application file for complete search history.

(56) References Cited

U.S. PATENT DOCUMENTS

| | | |
|---|---|---|
| 2013/0183243 A1 | 7/2013 | LaBelle et al. |
| 2014/0107450 A1* | 4/2014 | Simpson ............... A61B 5/1473 600/365 |
| 2014/0163346 A1* | 6/2014 | Pesantez ............ A61B 5/14532 600/347 |
| 2015/0177180 A1* | 6/2015 | Davis ................... G01N 27/026 205/780.5 |
| 2017/0234894 A1 | 8/2017 | LaBelle et al. |

OTHER PUBLICATIONS

A.G.E Saum, R.H Cumming, F.J Rowell, Use of substrate coated electrodes and AC impedance spectroscopy for the detection of enzyme activity, Biosensors and Bioelectronics, vol. 13, Issue 5, 1998, pp. 511-518, ISSN 0956-5663, https://doi.org/10.1016/S0956-5663(97)00129-2. (Year: 1998).*

Bisker G, Iverson NM, Ahn J, Strano Ms. A pharmacokinetic model of a tissue implantable insulin sensor. Adv Healthc Mater. Jan. 7, 2015;4(1):87-97. doi: 10.1002/adhm.201400264. Epub Jul. 31, 2014. PMID: 25080048; PMCID: PMC6438194. (Year: 2015).*

* cited by examiner

FIGS. 2A-C

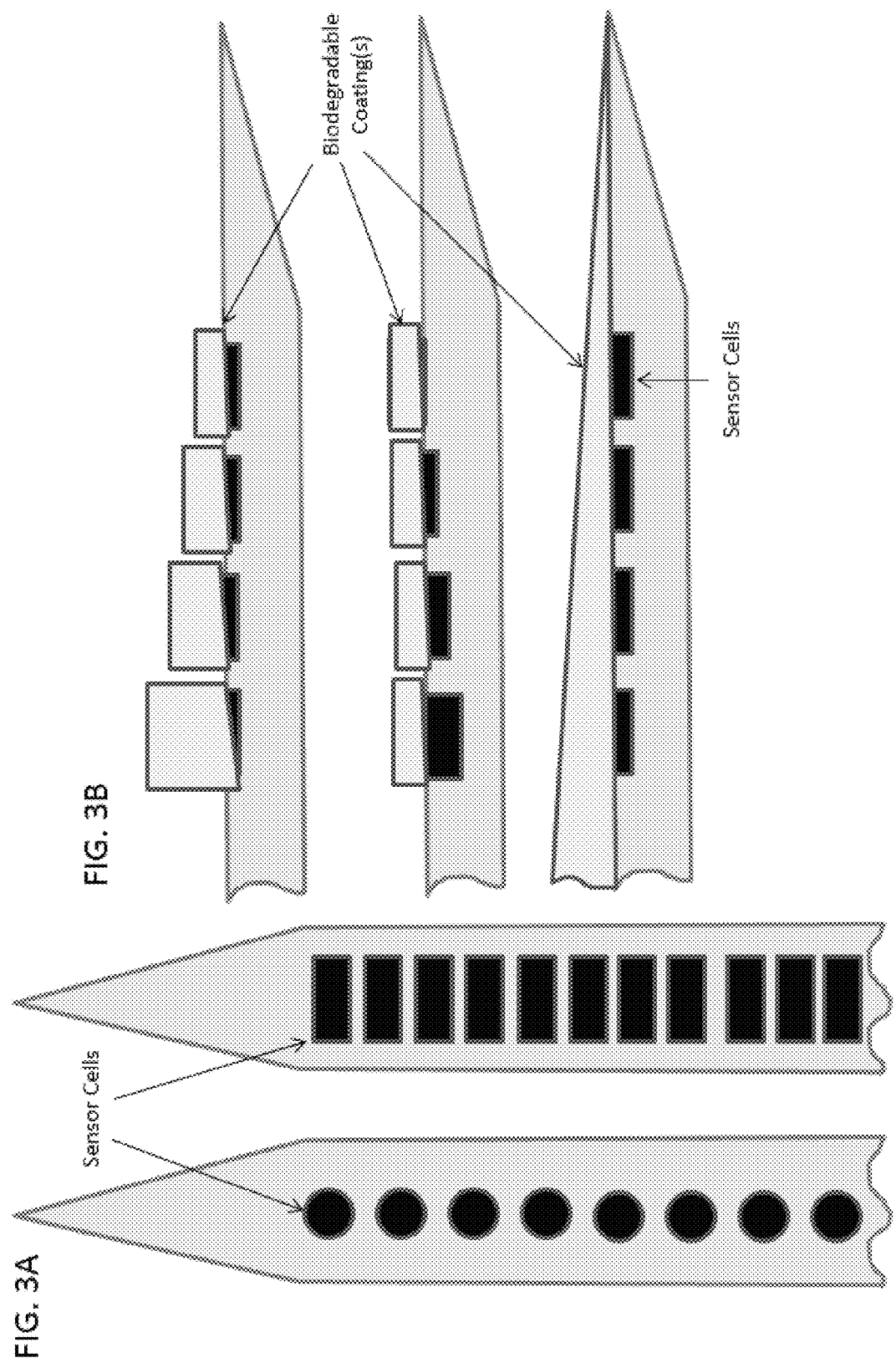

BIOSENSOR ARRAY FOR THE DETECTION OF ANALYTES

CROSS-REFERENCE TO RELATED APPLICATIONS

This application claims the benefit of U.S. Provisional Patent Application No. 62/589,066, filed on Nov. 21, 2017, the entire content of which is fully incorporated herein by reference.

TECHNICAL FIELD

Embodiments of the present disclosure relate generally to devices for detecting analytes in a subject. More particularly, the present disclosure provides a biosensor array that includes a plurality of sensor cells and a biodegradable coating to facilitate the detection of analytes in a subject.

BACKGROUND

Diagnosis and monitoring of various diseases often requires the detection and measurement of the concentration of one or more analytes in a subject. For example, the continuous measurement of analytes in biological fluids is of particular interest in the control and study of metabolic disorders, such as diabetes mellitus. Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological impairments associated with the deterioration of small blood vessels, for example, kidney failure, skin ulcers, or bleeding into the vitreous of the eye.

Conventionally, a person with diabetes uses a self-monitoring blood glucose monitor to obtain measurements of blood glucose levels. Such monitors typically require finger pricks to obtain blood samples for measurement, which can cause patient discomfort. Due to the lack of comfort and convenience associated with finger pricks, a person with diabetes normally only measures his or her glucose levels two to four times per day. This may lead to time intervals between measurements being spread far enough apart that the person with diabetes finds out too late of a hyperglycemic or hypoglycemic condition, sometimes incurring dangerous side effects. As such, continuously or intermittently operating sensors, including sensors implanted in the human body, are needed for improved management of diabetes and other disorders.

SUMMARY

Embodiments of the present disclosure relate generally to devices for detecting analytes in a subject. More particularly, the present disclosure provides a biosensor array that includes a plurality of sensor cells and a biodegradable coating to facilitate the detection of analytes in a subject.

Embodiments of the present disclosure include a biosensor array comprising a plurality of sensor cells for detecting an analyte in a subject. In accordance with these embodiments, the plurality of sensor cells comprise at least one electrode, at least one antibody immobilized on a surface of the at least one electrode, and a biodegradable coating in contact with the at least one antibody.

In some embodiments, the analyte is insulin. The antibody may be any antibody that binds to insulin. In some embodiments, the biodegradable coating comprises gelatin. In other embodiments, the biodegradable coating comprises one or more of polyglycolic acid (PGA), polylactic acid (PLA), or co-polymers thereof. In some embodiments, the sensor cells contain the biodegradable coating, and the biodegradable coating comprises varying degrees of thickness.

Embodiments of the present disclosure include methods of detecting an analyte in a subject. In accordance with these embodiments, the methods include implanting a disclosed biosensor array in the subject and detecting an analyte in the subject.

BRIEF DESCRIPTION OF THE DRAWINGS

FIGS. 3A-3B show an overview of biosensor arrays having multiple different configurations. Biosensor arrays can include sensor cells having any shape, including a generally circular shape (left) or a generally square/rectangular shape (right) (FIG. 3A). Biosensor arrays can include one or more biodegradable coatings within each sensor cells having varying degrees of thickness (top), or a continuous coating having varying degrees of thickness across multiple sensor cells (bottom); biosensor arrays can also include one or more biodegradable coatings having a substantially uniform thickness, with each underlying sensor cell and/or electrode having varying degrees of thickness/height (e.g., varying degrees of exposure to the coating) (middle).

FIG. 5A shows a Nyquist Overlay plot of increasing insulin concentration. FIG. 5B shows a Z" Overlay plot of increasing insulin concentration. FIG. 5C shows a calibration curve of insulin measured at 1758 Hz.

FIG. 6A shows a Nyquist Overlay plot of increasing insulin concentration. FIG. 6B shows a Z" Overlay plot of increasing insulin concentration. FIG. 6C shows a calibration curve of insulin measured at 146.5 Hz.

DETAILED DESCRIPTION

1. Definitions

Figure 1:
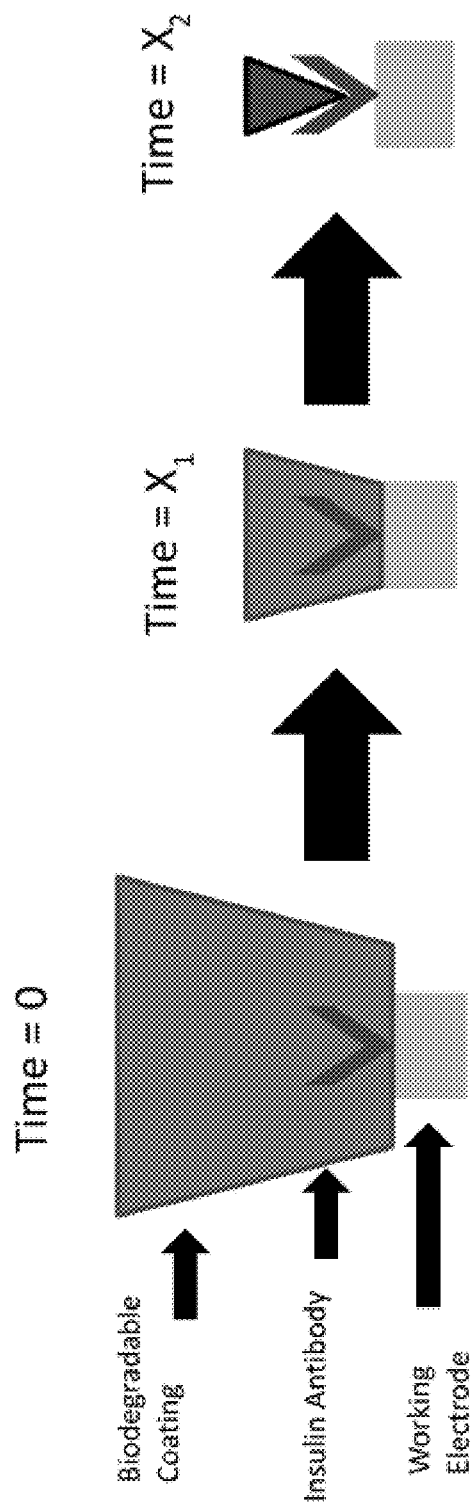
FIG. 1 shows a representative diagram of a design of the biosensor array. Each sensor cell can contain an insulin antibody immobilized to a surface of the working electrode. The insulin antibody can be in direct contact with a biodegradable material having a predetermined height or depth. The biodegradable material can degrade over time, as seen in the comparison of Time 0 to Time $X_1$ and time $X_2$. When the biodegradable material sufficiently degrades, the antibody binding site is exposed to the environment and may bind insulin.
Figure 2A:
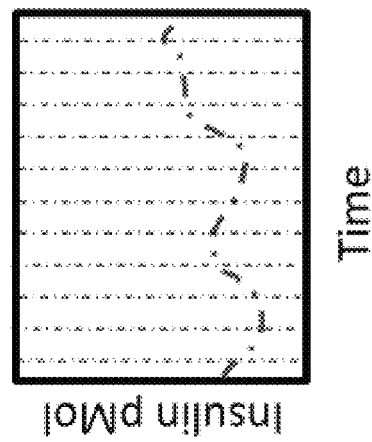
FIGS. 2A-2C show an overview of an array design and data collection method. The example biosensor array is square in shape and contains at least 72 individual sensor cells (FIG. 2A). Each sensor cell contains an insulin antibody immobilized to the surface of the working electrode. The insulin antibody is in direct contact with a biodegradable material of a predetermined height or depth. Each sensor cell may contain a biodegradable material of varying degrees of thickness such that the antibody binding site is exposed to the environment at varying time points (FIG. 2B). Sets of antibodies can be exposed to the environment at varying time points. Data collected at these varying time points may be interpolated to allow for a smooth curve displaying levels of insulin in the subject (FIG. 2C).
Figure 2C:
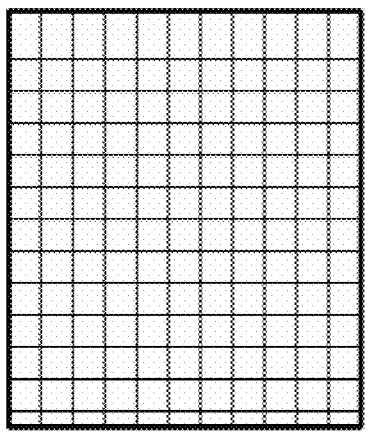
Figure 2B:
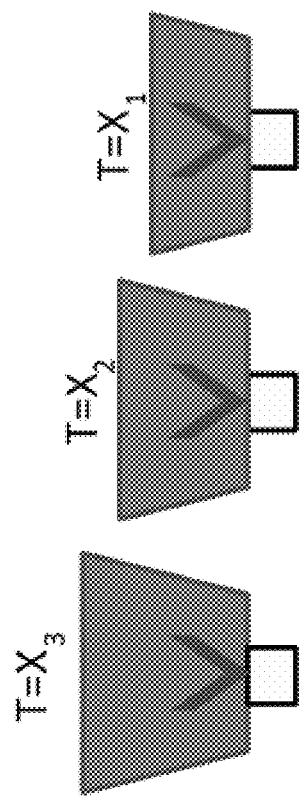

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "analyte," as used herein refers to a substance or chemical constituent in a biological fluid.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies, and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA and IgY), class (for example, IgG1, IgG2, IgG3, IgG4, IgA1 and IgA2) or subclass.

"Biocompatible" generally refers to a material and any metabolites or degradation products thereof that are generally non-toxic to the recipient and do not cause any significant adverse effects to a subject.

The terms "operably connected," or "operably linked," as used interchangeably herein, refer to one or more components being linked to another component(s) in a manner that allows transmission of signals between the components.

As used herein, the term "polymer" refers to a relatively high molecular weight organic compound, natural or synthetic, whose structure can be represented by a repeated small unit, the monomer (e.g., polyethylene, rubber, cellulose), which can be joined to form a larger polymeric matrix. Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

2. Biosensor Array

Before any embodiments of the present disclosure are explained in detail, it is to be understood that the present disclosure is not limited in its application to the details of construction and the arrangement of components set forth in the following description or illustrated in the accompanying drawings. The present disclosure is capable of other embodiments and of being practiced or of being carried out in various ways.

Other aspects of the invention will become apparent by consideration of the detailed description and accompanying drawings.

Embodiments of the present disclosure relate generally to devices for detecting analytes in a subject. Embodiments of the present disclosure include a biosensor array comprising a plurality of sensor cells for detecting an analyte in a subject. In accordance with these embodiments, the plurality of sensor cells comprise at least one electrode, at least one antibody immobilized on a surface of the at least one electrode, and a biodegradable coating in contact with the at least one antibody.

In some embodiments, the biosensor array may comprise a plurality of sensor cells. The biosensor array may include any suitable number of sensor cells for detection of an analyte of interest in a subject. The biosensor array may include at least about 72 sensor cells. For example, the biosensor array may comprise at least about 72, at least about 81, at least about 90, at least about 100, at least about 110, at least about 121, at least about 132, or at about least 144 sensor cells. In some embodiments, the biosensor array include about 96 sensor cells. In some embodiments, the plurality of sensor cells may be arranged such that the biosensor array is rectangular in shape. For example, the plurality of sensor cells may be arranged such that the biosensor array may be square in shape. In other embodiments, the plurality of sensor cells may be arranged such that the biosensor array is cylindrical in shape.

Embodiments of the present disclosure include a biosensor array comprising a plurality of sensor cells having at least one electrode. In some embodiments, the at least one electrode is a working electrode. The plurality of sensor cells may also include three electrodes. For example, the plurality of sensor cells may include a working electrode, a counter electrode, and a reference electrode. The at least one electrode may also include any suitable conductive material. For example, the electrode may comprise platinum, black platinum, gold, silver, palladium, nickel, copper, mesoporous carbon, screen printed carbon, glassy carbon, indium tin oxide, and the like.

In some embodiments, the at least one electrode may be any suitable size and configuration to enable detection of the analyte. For example, the electrodes may be microelectrodes. As another example, the electrodes may be nanoelectrodes. The electrodes may be solid electrodes. The electrodes may be interdigitated electrodes. For example, the electrodes may be interdigitated electrodes may be spaced on any suitable substrate. Suitable substrates include glass, ceramic, synthetic polymers, plastics, silica, alumina, and the like. As would be appreciated by one of skill in the art, any suitable spacing between the interdigitated electrodes may be used, dependent on the size and shape of the substrate and the size and shape of the biosensor array.

In some embodiments, the plurality of sensor cells may include a two electrode configuration comprising a counter electrode and a reference electrode. For example, in a two electrode configuration, the counter electrode and the reference electrode can be shorted on one of the electrodes while the working electrode can be shorted on the opposite electrode. The potential across the plurality of sensor cells can then be measured, which includes contributions from the counter electrode and also an electrolyte, if applicable. As would be appreciated by one of ordinary skill in the art based on the present disclosure, a two electrode configuration is commonly used with energy storage or conversion devices like batteries, fuel cells, photovoltaic panels, and the like. A two electrode configuration can also be used for measurements of ultrafast dynamics of electrode processes or electrochemical impedance measurements at high frequencies (e.g., >100 kHz).

In other embodiments, the plurality of sensor cells may include a three electrode configuration. For example, in a three electrode configuration, the sensors cells may comprise three separate electrodes: a working electrode, a counter electrode, and a reference electrode. In other embodiments, the plurality of sensor cells may include a four electrode configuration. For example, in a four electrode configuration, the plurality of sensor cells comprise two working electrodes, a counter electrode, and a reference electrode.

In some embodiments, the biosensor array included at least one antibody immobilized on a surface of the at least one electrode. In accordance with these embodiments, the antibody may be immobilized on a surface of the working electrode. The antibody may be any suitable antibody for detecting or binding an analyte in a subject. For example, the antibody may bind insulin. In some cases, multiple antibodies may be used to detect an analyte, such as a capture antibody and a detection antibody. The capture antibody may bind the analyte, whereas the detection antibody may bind the antibody-analyte complex. The detection antibody may further include a means for detecting and/or quantifying the complex, such as a reporter molecule.

In some embodiments, the biosensor array includes a biodegradable coating in direct contact with the at least one antibody. The biodegradable coating may be any suitable biocompatible material that degrades at a defined rate within an in vivo environment. In some embodiments, the biodegradable coating is gelatin. In some embodiments, the biodegradable coating may be a biodegradable polymer. For example, the biodegradable coating may be polylactic acid (PLA), polyglycolic acid (PGA), and copolymers thereof such as polylactide-co-glycolide (PLGA). Additional potential biodegradable polymers include polymers and copolymers of polyanhydride, polyhydroxy acids, polylactones, polytrimethylene carbonate, polyglycolic acid-co-polyglycolic acid, polyorthocarbonate, polycaprolactone, polylactide, polyglycolide, polycarbonates, polyamides, polyamino acids, polyorthoesters, polyacetals, polycyanoacrylates, polyetheresters, polydioxanones, polyalkylene alkylates, copolymers of polyethylene glycol and polyortho ester, degradable polyurethanes and copolymers, and blends thereof. Other suitable biodegradable materials include natural resources such as starch, cellulose, and soy protein. For example, suitable biodegradable materials include starch, cellulose, hemicellulose, chitin, alginate, hyaluronic acid, gellan gum, seed husk, and the like.

In certain embodiments, the biodegradable coating may be a blend of one or more biodegradable polymers. In some embodiments, the biodegradable coating may be a biodegradable gel or similar material. For example, the biodegradable coating may be a crosslinked biodegradable hydrogel network like fibrin glue or fibrin sealant. Each of the plurality of sensor cells may include the same biodegradable coating. The plurality of sensor cells may include varying biodegradable coatings. For example, each row of the biosensor array may include a different biodegradable coating.

In some embodiments, the biocompatible material may initially cover the antibody binding region, such that the antibody is unable to bind to an analyte of interest. Upon degradation of the biodegradable material, the antibody binding site is exposed to the in vivo environment, which enables analyte binding. In such embodiments, degradation of the biodegradable material and exposure of the antibody is directly proportional to analyte detection. The sensor cell is thus considered "activated" when the antibody binding site is exposed to the in vivo environment. The rate of degradation of the biodegradable material may be selected to allow for different sets of sensor cells to become activated at varying time points. For example, predetermined sets of sensor cells may include biodegradable materials with different degradation rates, such that the antibody binding sites for each set of sensor cells are exposed to the environment at varying time points.

As another example, the biodegradable material may be the same across the plurality of sensor cells but the thickness of the biodegradable material can be adjusted to allow different sets of sensor cells to become activated at varying time points. In such embodiments, the thickness of the biodegradable coating may vary across the plurality of sensor cells. For example, each row of sensor cells within the biosensor array may comprise varying degrees of thickness of the biodegradable coating. As another example, each column of sensor cells within the biosensor array may include varying degrees of thickness of the biodegradable coating. Sensor cells that include a thin layer of biodegradable coating can become activated after a shorter time period in vivo compared to sensor cells that include a thicker layer of a biodegradable coating.

Embodiments of the present disclosure also include systems configured to operate one or more biosensor arrays, also referred to as biosensor array systems. A biosensor array system can include an electronic circuit having a microcontroller or a microcomputer-based system, which functions to calculate and record measurement results, such analyte detection and/or antibody binding. Biosensor arrays can also include a source of power, such as one or more batteries, or any other suitable power source and/or power supply, and can be electrically coupled to an integrated measurement system and an electronics circuit. An optional display can be configured to indicate a presence or an absence of one or more detectable parameters. In other embodiments, with or without a display, a measurement can be sent via a wired or wireless connection to another computer or computer network. Biosensor array system components may be interconnected or communicate with other components using electrical, electronic, or electromagnetic signals (e.g., optical, radio frequency, digital, analog or other signaling scheme). Biosensor array systems can also include software programs or reconfigurable firmware or emulation logic devices to verify, model, simulate, or analyze stored or raw data.

3. Methods of Analyte Detection

Embodiments of the present disclosure include methods for detecting an analyte in a subject. The method may comprise implanting the biosensor array into a subject and detecting an analyte in the subject. In some embodiments, the biosensor array may be implanted subcutaneously. In accordance with these embodiments, the size of the biosensor array may be limited to minimize potential discomfort to the subject. In some embodiments, the biosensor array may be about 1-100 mm thick. For example, the biosensor array may be about 1 to about 100 mm thick, about 1 to about 50 mm thick, about 1 to about 25 mm thick, about 1 to about 10 mm thick, about 1 to about 5 mm thick, or about 5 to about 10 mm thick. In some embodiments, the biosensor array may be rectangular in shape with dimensions of about 10 mm to about 100 mm for length and width, respectively. For example, the biosensor array may square in shape with a length of about 25 mm and a width of about 25 mm. In other embodiments, the biosensor array may be about 0.1 mm to about 10 mm thick, about 0.1 mm to about 5 mm thick, or about 0.1 mm to about 1 mm thick.

In some embodiments, the analyte is insulin. However, the analyte may be any substance or chemical constituent in a biological fluid. Analytes can include naturally occurring substances, artificial substances, metabolites, or reaction products. In some embodiments, the analyte may be a naturally occurring or endogenous substance present in biological fluid of a subject. For example, the analyte may be a metabolic product, a hormone, an antigen, an antibody, and the like. Illustrative analytes include but are not limited to glucose, lactate, salts, sugars, proteins, fats, vitamins, and hormones that naturally occur in biological fluids. In other embodiments, the analyte can be introduced into the body or exogenous analytes. For example, the analyte may be a contrast agent for imaging, a radioisotope, a chemical agent, a fluorocarbon-based synthetic blood, a drug or pharmaceutical composition, or a metabolic product of a drug of pharmaceutical composition.

In some embodiments, the biosensor array may detect the analyte in a subject by electrochemical impedance spectroscopy (EIS). In such embodiments, an alternating current may be transmitted to the sensor cell through the counter electrode. The alternating current potential may be transmitted through the counter electrode at varying frequencies. Additionally, as described above, a two electrode system comprising a counter electrode and a reference electrode may also be used. In some embodiments, the frequency may range from about 1 Hz to about 100 kHz. For example, the frequency may be about 1 Hz to about 100 kHz, about 10 Hz to about 10 kHz, about 100 Hz to about 1000 Hz, about 200 Hz to about 900 Hz, about 300 Hz to about 800 Hz, about 400 Hz to about 700 Hz, or about 500 Hz to about 600 Hz. In some embodiments, the voltage bias may range from about 1 mV to about 10 mV. For example, the voltage bias may be about 2 mV to about 10 mV, about 4 mV to about 10 mV, about 6 mV to about 10 mV, about 8 mV to about 10 mV, about 2 mV to about 8 mV, about 4 mV to about 6 mV, or about 5 mV to about 10 mV. The resulting current may be measured at the working electrode with respect to the reference electrode, and used to calculate impedance as set forth in Equation 1 below:

$$Z=E/I \qquad \text{Equation 1:}$$

Where Z=impedance, E=Frequency-dependent potential, and I=Frequency-dependent current.

Impedance is a complex number that has both real and imaginary parts. This function is described by equation 2 below.

$$Z = Z_0 \frac{\sin(wt)}{\sin(wt+\phi)} \qquad \text{Equation 2}$$

Where $Z_0$=magnitude, w=angular frequency=$2\pi f$, t=time, and ϕ=phase shift.

Using an expression analogous to Ohm's Law, impedance of the system may be calculated and expressed as magnitude and phase shift. Using Euler's relationship, this platform function may be simplified as shown in Equation 3 below.

$$Z=Z_0(\cos(\emptyset)+j\sin(\emptyset)) \quad \text{Equation 3:}$$

Where j is an imaginary number.

Each of these outputs may be expressed as a Randel's circuit. The equivalent transfer function for a Randel's circuit is shown in Equation 4 below:

$$Z(w) = Z'(w) + jZ''(w) = R_{sol} + \frac{R_{et}}{1+(wR_{et}C_{dl})} - \frac{wR_{et}^2 C_{dl}}{1+(wR_{et}R_{dl})^2}$$

Where $R_{sol}$ is the solution resistance, $R_{et}$ is resistance of electron transfer, and $C_{dl}$ is the double layer capacitance of the system. For Equation 4, the top of the biodegradable material is considered the top layer of the double layer system and the base of the working electrode is considered the bottom layer of the double layer system, Capacitance is inversely related to the distance between these two layers. As such, degradation of the biodegradable layer results in a decreased distance between the two layers of the double layer system and a subsequent increase in the double layer capacitance of the system.

In some embodiments, the double layer capacitance of the system may be used to determine which sensor cells are about to be activated (i.e., the antibody bound to the working electrode is nearly exposed to the in vivo environment). In such embodiments, when the double layer capacitance drops to a set value transmission of the alternating current potential through the counter electrode may be initiated. In some embodiments, the double layer capacitance may also be measured and used for quality control of the device. In such embodiments, calculation of the double layer capacitance for each of the plurality of sensor cells may be used to indicate when the biodegradable material for each of the plurality of sensor cells is mostly or completely degraded.

In other embodiments, constant phase element (CPE) can be used as an alternative for or in addition to a capacitor. Constant phase elements can be used in equivalent circuit modelling and data fitting of electrochemical impedance spectroscopy (EIS) data. A CPE can be considered a device having one or more characteristics that are between a resistor and a capacitor. CPEs are used when one or more properties of a system are not homogeneous, or that there is some distribution (dispersion) of the value of some physical property of the system. For example, CPEs can be used with the biosensor arrays of the present disclosure, which include varying thickness of biodegradable materials.

In some embodiments, an alternating current may be transmitted to the sensor cell through the counter electrode and the resulting impedance may be calculated at the working electrode with respect to the reference electrode. In such embodiments, the impedance will decrease as the biodegradable layer degrades over time. Upon sufficient degradation of the biodegradable layer, the analyte may bind to the antibody immobilized to the surface of the working electrode, and a rapid increase in impedance should occur. The calculated impedance may be used to derive the concentration of analyte in the subject. In some embodiments, the concentration of analyte may be derived using a calibration curve. The calibration curve may be determined by comparing set insulin levels to the calculated impedance of the working electrode with respect to the reference electrode. Additionally, as would be appreciated by one of skill in the art based on the present disclosure, related transfer functions, such as but not limited to, admittance, capacitance, and modulus, can also be used as bases for determining calibration curves.

In some embodiments, EIS measurements may be performed regularly to enable continuous or regular detection of an analyte in a subject. In such embodiments, EIS measurements may be performed about every 1-60 minutes. For example, EIS measurements may be performed about every 1-60 minutes, about every 10-50 minutes, about every 20-40 minutes, or about every 30 minutes. In some embodiments, continuous or regular detection of an analyte in a subject may be obtained until the lifetime of the biosensor array is expired. The lifetime of the biosensor array will depend on the number of sensor cells in the biosensor array and the material and thickness of the biodegradable coating. In some embodiments, the lifetime of the biosensor array may be about at least 1 week. For example, the lifetime of the biosensor array may be at least 1 week, at least 2 weeks, at least 3 weeks, at least 4 weeks, at least 2 months, at least 3 months, or at least 6 months.

In some embodiments, the plurality of sensor cells may be operably linked to an external device. The external device may record and/or display the data collected by the biosensor array. For example, the working electrode may be used to detect current and convert that information into a signal. The signal may then be transmitted to an external device (i.e., the electrode is "operably linked" to the external device), which may convert the signal into a numerical value for impedance. This numerical value for impedance may then be used to derive the concentration of analyte in a sample using a calibration curve. The plurality of sensor cells may be operably linked to an external device to allow for signal transmission by a variety of methods. For example, signal transmission may occur through a Bluetooth low energy system.

EXAMPLES

The following examples are illustrative of disclosed methods. In light of the present disclosure, those of skill in the art will recognize that variations of these examples and other examples of the disclosed method would be possible without undue experimentation.

Example 1

Detection of Insulin

A biosensor array having 96 individual sensor cells may be used to detect insulin in a human subject. The sensor cells may comprise a working electrode, a reference electrode, and a counter electrode. An insulin antibody may be immobilized to a surface of the working electrode. Each row of sensor cells within the biosensor array may contain a biodegradable coating of varying thickness, such that each sensor cell within the row becomes activated at approximately the same time but the varying rows of the biosensor array are activated at different time points.

The biosensor array may be implanted subcutaneously into the subject by a trained physician. The initial capacitance of the biosensor array may be measured to determine the distance between the base of the working electrode and the top of the biodegradable material. Subsequent capacitance measurements may be performed until the capacitance drops to a set value, which indicates that a row of sensor cells is about to become activated. Electrochemical impedance spectroscopy measurements may then begin. EIS measurements may be obtained every 30 minutes, and the results may be compared to a calibration curve to calculate insulin concentration over time.

Example 2

Glutaraldehyde (GA) Protocol on Carbon Screen Printed Electrodes

The Glutaraldehyde (GA) protocol was used for the immobilization of the insulin antibody onto the sensor surface.

Biosensor Fabrication Procedure:

Carbon screen printed electrodes (Zensors) were used. The protocol was commonly run in batches of 32. Zensors were first taped to the bottom of a petri dish with working electrodes exposed. 10 µL of 60.47 nM Insulin Antibody was pipetted onto each working electrode. Zensors were then dried in a Thermocenter at room temperature. After one hour, Zensors were removed from the Thermocenter regardless of dryness. 1 mL of 25% w/w Glutaraldehyde (GA) was evenly spread on top of the petri dish. The petri dish was combined with Zensors on top and upside down. The petri dish was then sealed with PARAFILM® M and put on shake plate for one hour for chemical vapor deposition. The petri dish was disassembled and Zensors were dried face up in the Thermocenter at room temperature for 30 minutes. Zensors were then soaked in 2 mL of 1 M TRIS/HCl for 25 minutes. Zensors were rinsed and stored in PBS. Prior to testing, Zensors were dried with compressed air until dry.

A formal potential of 0.15V was used for EIS. The optimal frequency was determined to be about 25.7-37.65 Hz for 2 samples. The lowest R-square values (RSQ) was 0.6223 but remaining RSQs were between 0.69-0.74. Sensors that did not dry completely on the antibody step produced the worst data.

Determination of Optimal Binding Time. The Zensors were prepared as described above. The testing protocol used was as follows: For Method #1, 5 µL insulin and 45 µL 10 mM ferricyanide were pipetted onto the Zensor and let to sit for 1-3 minute. For Method #2, 30 µL double insulin concentration and 30 µL ferricyanide were added and mixed on the electrode surface creating the normal insulin concentration and 10 mM ferricyanide. EIS measurements were taken from 0-8 min. Based on the experiments, 1 min incubation was determined to be optimal binding time (data not shown).

Figure 7A:
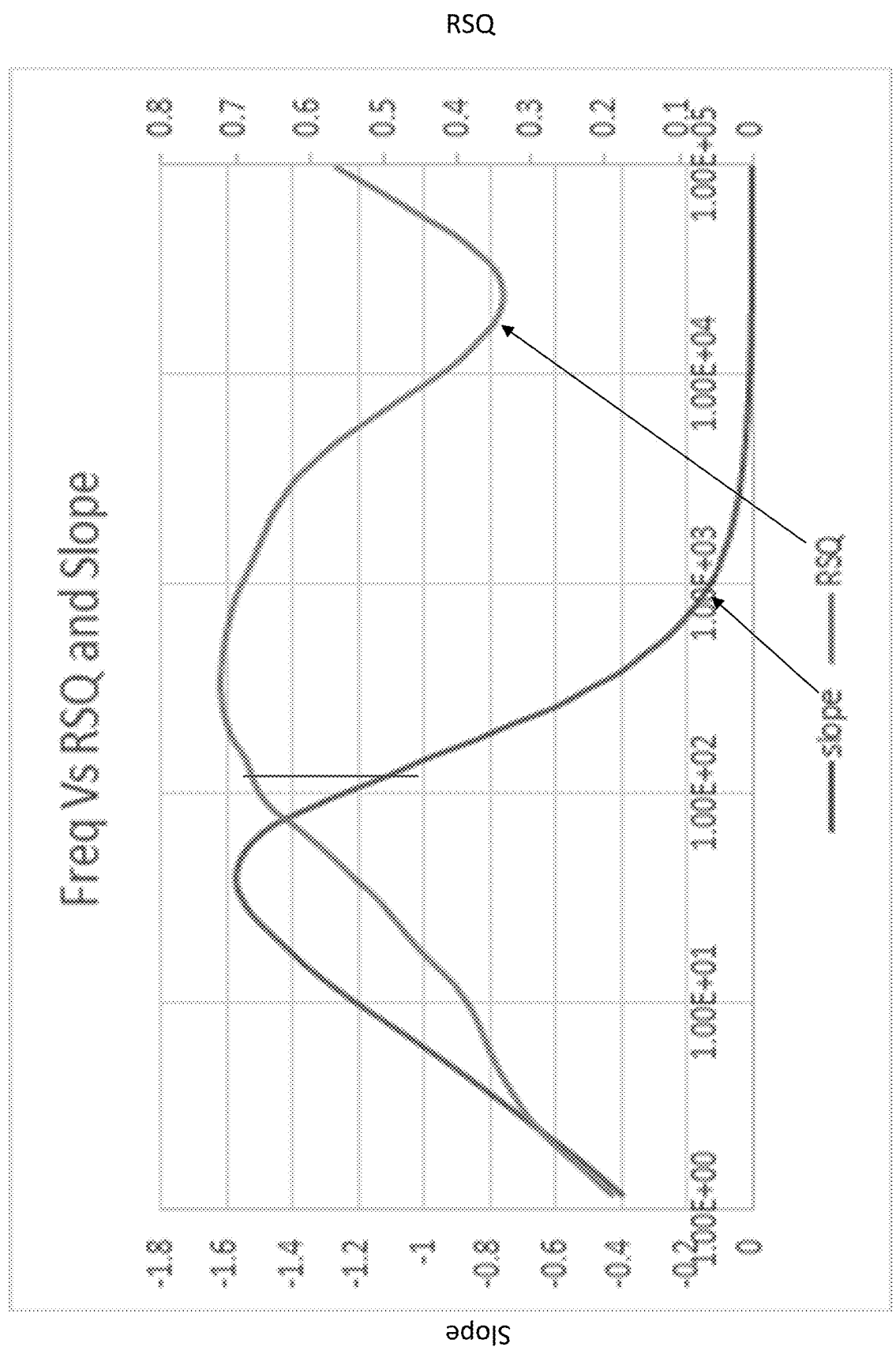
FIG. 7A shows the logarithmic fit (slope) and −RSQ values by fitting the imaginary impedance against target insulin concentrations across the frequency sweep.
Figure 7B:
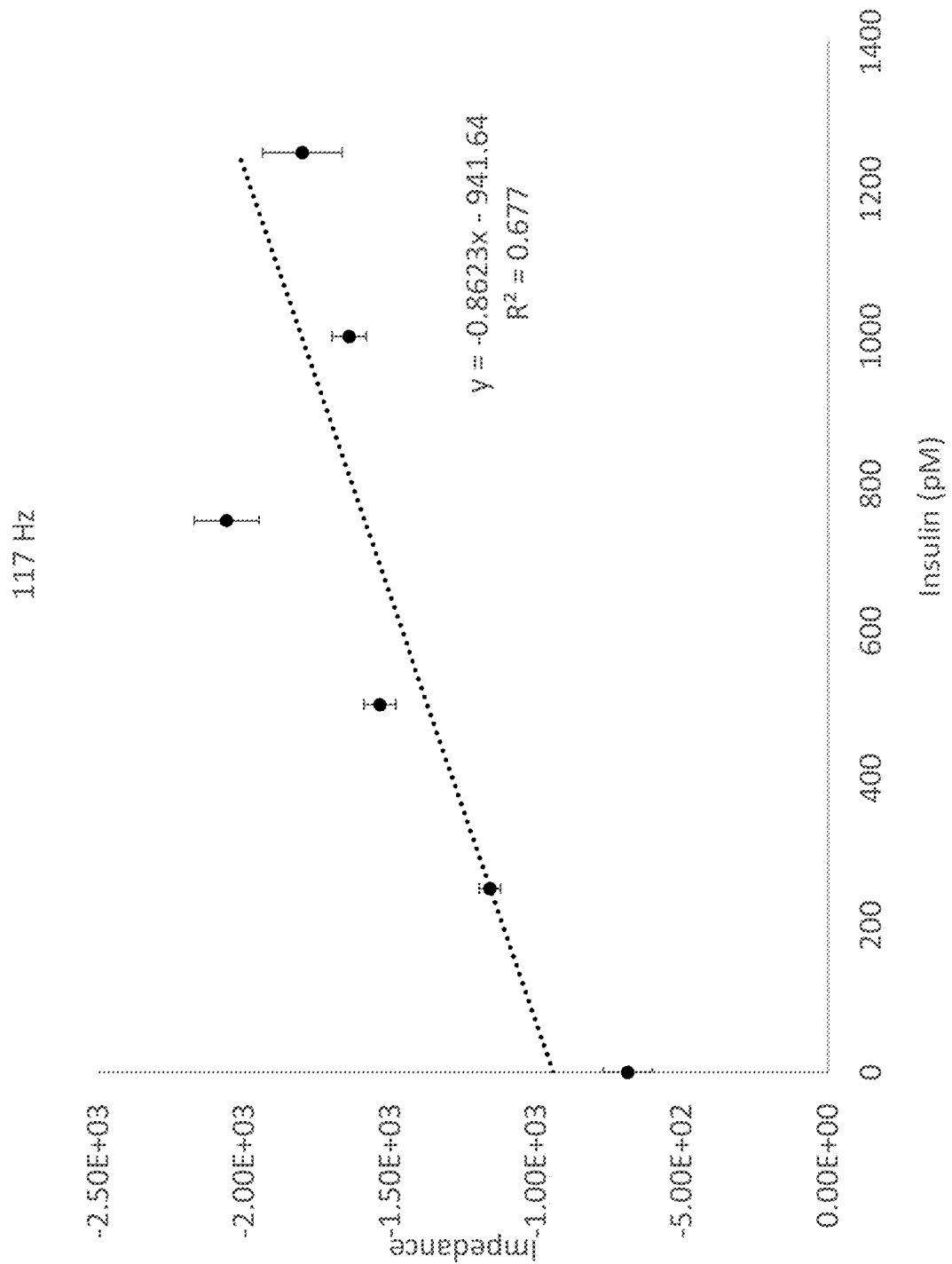
FIG. 7B shows the relationship between impedance response and its associated insulin concentration at a concentration gradient taken at a frequency of 117 Hz.
Figure 8A:
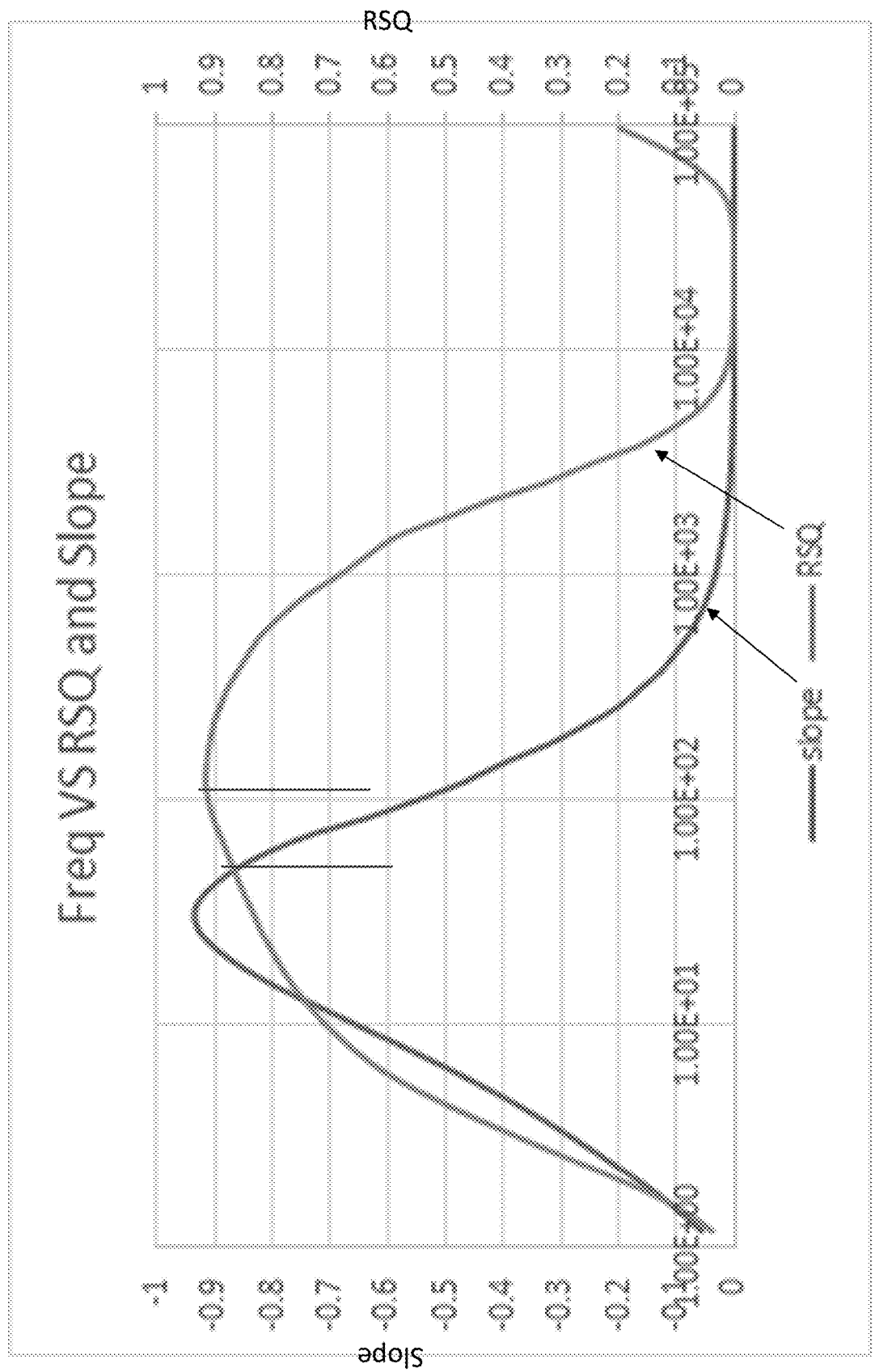
FIG. 8A shows the logarithmic fit (slope) and −RSQ values by fitting the imaginary impedance against target insulin concentrations across the frequency sweep.
Figure 8B:
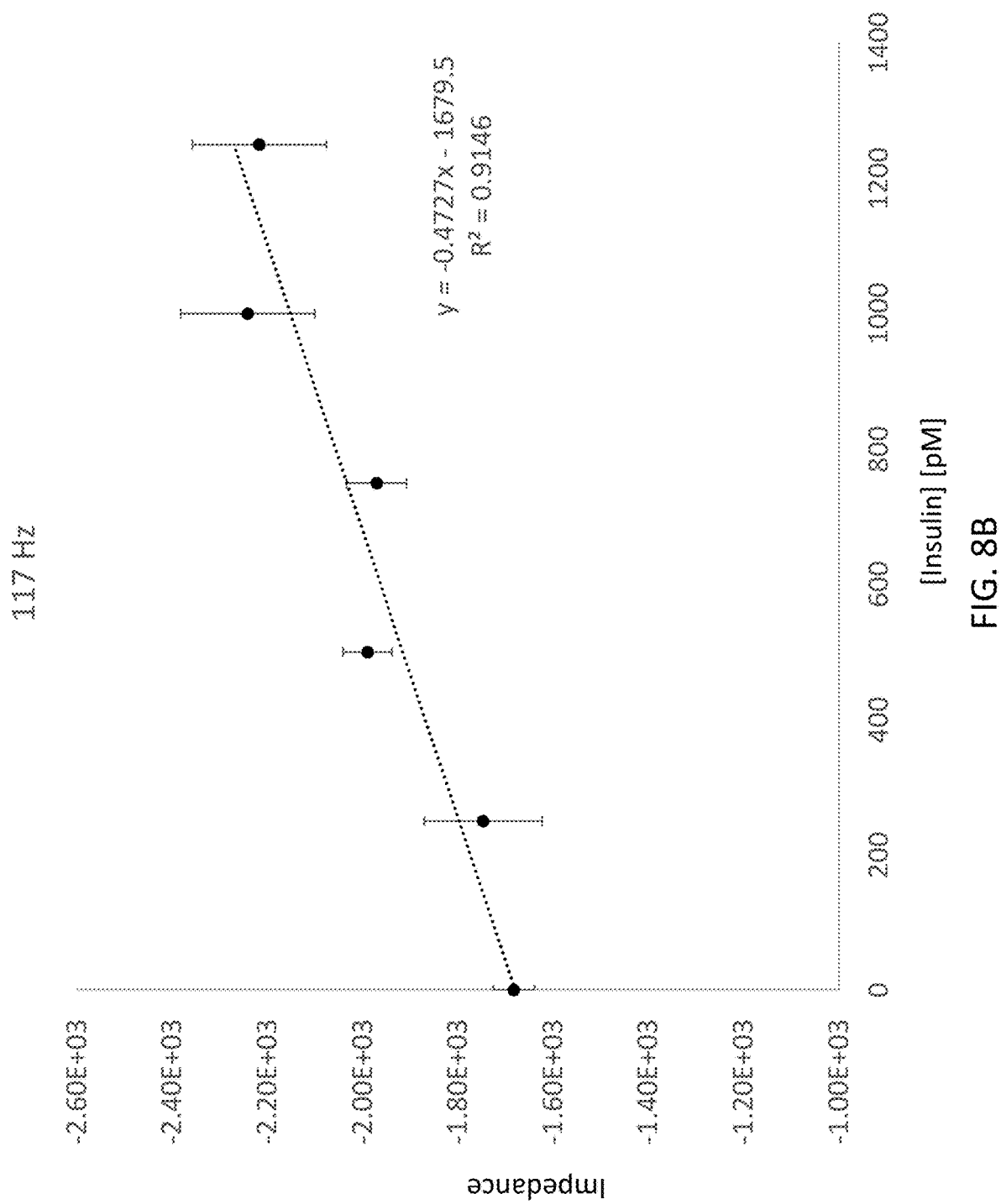
FIG. 8B and FIG. 8C show the relationship between impedance response and its associated insulin concentration at a concentration gradient taken at a frequency of 117 Hz (FIG. 8B) and 46.5 Hz (FIG. 8C).
Figure 8C:
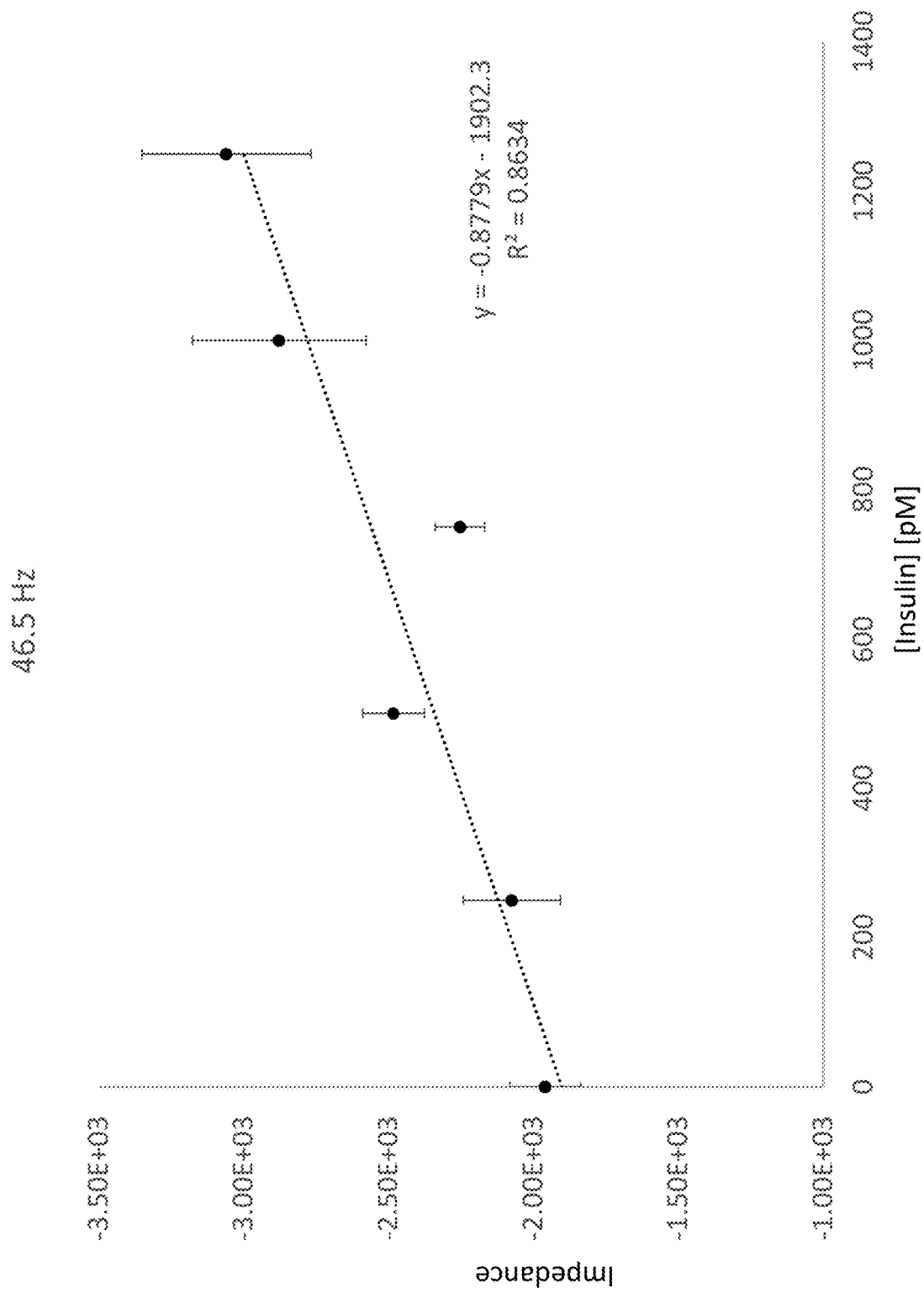

The experiments were replicated to verify the 1 minute binding time and to ensure the effectiveness of the GA process for antibodies. Results from EIS are shown in FIGS. 7A-7B and FIGS. 8A-8C. FIG. 7A and FIG. 8A indicate the optimal frequency was 117 Hz (indicated by vertical lines). Taken together, the data show that insulin was reliably measured with the sensor and the process was replicable. The GA protocol was used to immobilize antibodies on the sensor surface.

The prepared Zensors, as described above, can be coated with a biodegradable coating prior to EIS. For example, the Zensors can be coated with 20 µL, 25 µL, 30 µL, or 100 µL of gelatin and allowed to sit overnight at 4° C. prior to EIS.

Example 3

Mercaptohexadecanoic Acid (MHDA) Protocol on Gold Screen Printed Electrodes

Biosensor Fabrication Procedure:

Sensors based on gold screen printed electrodes (Zimmer & Peacock) were polished in figure eight's with aluminum oxide. Sensors were rinsed and then stored in deionized (DI). Sensors were taped with the working electrode exposed and other electrodes covered. Sensors were electroplated for 1 min then stored in DI again. Sensors were soaked in 1.5 mL of 1 mM 16-mercaptohexadecanoic acid (MHDA) for one hour in a dark environment. Sensors were rinsed with DI and stored dry overnight in a dark environment. 6 µL of 40 mM ethyl-3-(3-dimethylaminopropyl) carbodiimide hydrochloride (EDC)/N-hydroxysuccinimide (NHS) were added to each sensor and incubated for 1 hour in a wet environment. 6 µL of 100.83 nM insulin antibody were added to the sensor surface and incubated for 1 hour in a wet environment. 6 µL of 10% Ethanolamine was added to each sensor and incubated in a semi-wet environment for 30 minutes. Sensors were then rinsed and stored in DI.

Tape was removed and sensors were left to air dry completely prior to testing. For EIS, 5 µL of a sample containing insulin was added for one minute then 45 µL of 10 mM ferricyanide was added. EIS was performed with a formal potential of −0.154 V. Imaginary impedance was used for analysis.

The sensors can be coated with a biodegradable coating prior to EIS. For example, the sensors can be coated with 20 µL, 25 µL, 30 µL, or 100 µL of gelatin and allowed to sit overnight at 4° C. prior to EIS.

Example 4

Degradable Hydrogel on Gold Disc Electrodes

Biosensor Fabrication Procedure:

Gold disk electrodes (GDEs) were polished using alumina oxide and a Buehler felt pad. GDEs were then sonicated for 15 minutes. Cyclic voltammetry was performed for each GDE, and formal potential for each bare GDE was calculated. 1 mM 16-Mercaptohexadecanoic acid (MHDA) was prepared in ethanol as per immob calculator on shared drive. 100 µL of the 1 mM MHDA was pipetted into each GDE cap. The GDE was then covered with PARAFILM® M and allowed to sit in a dark cabinet for one hour at room temperature. GDEs were then rinsed with deionized (DI) water and a clean pipette tip covered in PARAFILM® M was added to each GDE. The GDEs were left to sit in a cabinet overnight at room temperature.

EDC/NHS/PBS solution was created using 80 mM 1-ethyl-3-(3-dimethylaminopropyl)carbodiimide hydrochloride (EDC), 10 mM N-hydroxysuccinimide (NHS), and Phosphate-buffered saline (PBS). 100 µL of the EDC/NHS/PBS solution was pipetted into each GDE cap. The GDE cap was subsequently stored at 4° C. for 1 hour.

100 µL of 60.47 nM anti-insulin antibody concentration was pipetted into each GDE cap and let sit in the 4° C. fridge for 1 hour.

99% ethanolamine was diluted down to 1% ethanolamine in DI water. 100 µL of the 1% ethanolamine solution was pipetted into each antibody-coated GDE cap and subsequently stored at 4° C. for 30 minutes.

Using Knox unflavored gelatin, liquid gelatin was prepared and cooled to room temperature. After cooling, 20 µL, 25 µL, 30 µL, or 100 µL of gelatin was pipetted at an angle into the antibody-coated GDE caps to form the gelatin coated GDE. The gelatin coated GDEs were stored at 4° C. overnight so the gelatin could solidify.

Biosensor Experimental Procedure:

A cap with Ag/AgCl reference electrode and Pt counter electrode was placed onto the gelatin coated GDE. 100 µL of the desired antibody concentration was pipetted onto working electrode. 100 µL of 20 mM ferricyanide was pipetted onto the working electrode. Alternating current impedance was performed at the formal potential found for each bare GDE. The cap was removed and the GDE was rinsed with PBS. The GDE was rinsed at the center and was not rinsed directly onto the working electrode. This process was repeated for each sensor and each desired insulin concentration.

Figure 4:
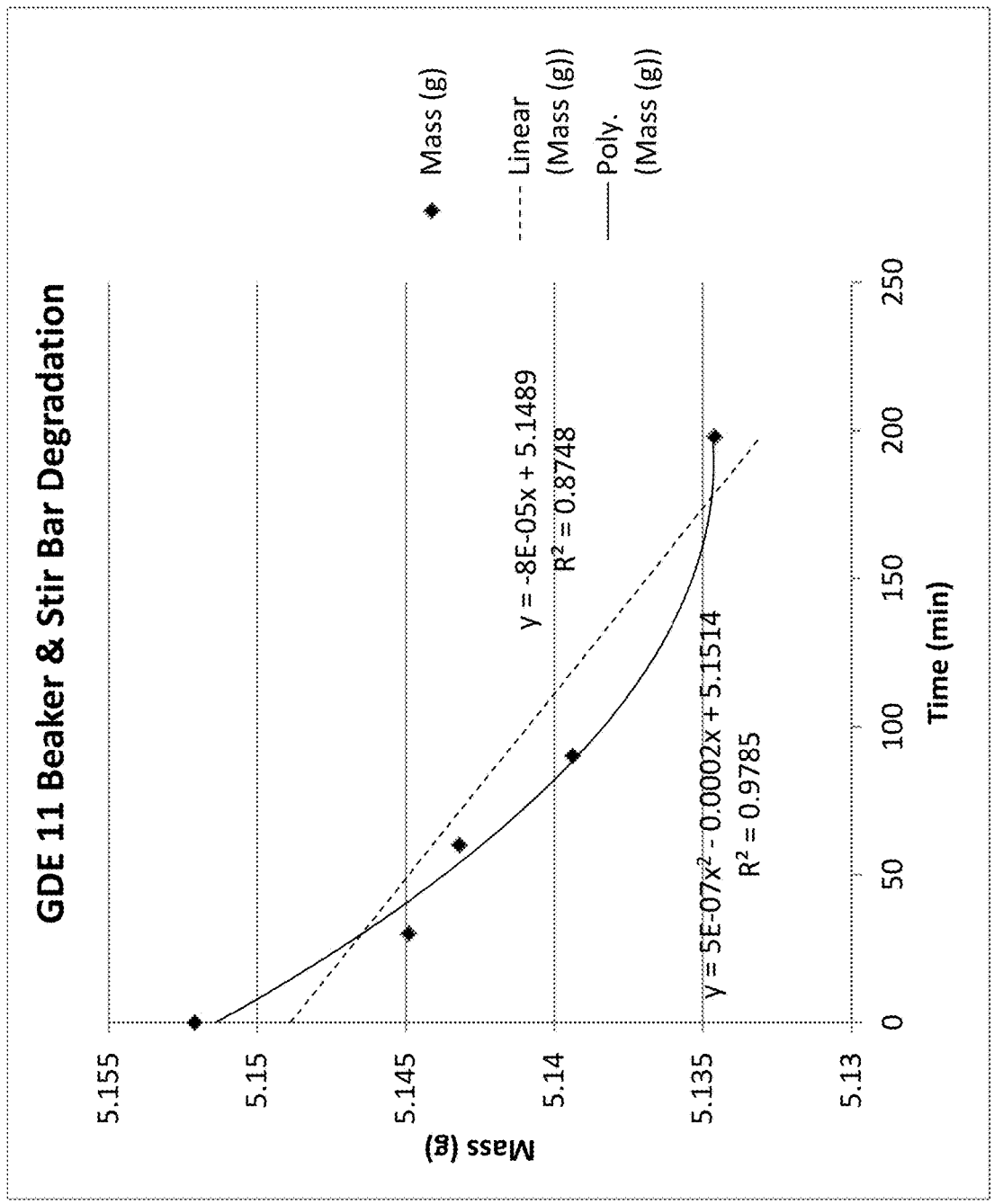
FIG. 4 shows a time model of degradation of the gelatin coating.

Gelatin Degradation Measurement:

A single GDE, referred to as GDE 11, was massed before and after the gelatin coating was applied. GDE 11 was placed into a beaker containing 200 mL of DI water. A stir bar was in the beaker and the stir plate was set to 200 rpm. The GDE was placed electrode side down so that it made contact with the water. At t=30, t=60, t=90, and t=200 min intervals, the GDE was removed from the beaker, allowed to air dry on low air, massed, and recorded. This procedure was used to create a time model of degradation based off change in mass. The results are shown in FIG. 4.

Electrochemical Impedance Spectroscopy:

50 mL of 10 mM ferricyanide was prepared and transferred to a 50 mL beaker. Black electrical tape was applied to the beaker to prevent light from penetrating the beaker. Ag/AgCl and Pt electrodes were carefully secured to the beaker such that the electrodes were touching the solution and could be connected to the CHI alligator clips. A stir bar was added into the 50 mL beaker, which was then placed on the stir plate set to stir at 200 rpm. Gelatin coated electrodes were placed in the beaker using a plastic GDE holder.

One GDE was tested at a time by clipping the green alligator clip to the desired working electrode. The FP was changed in between each tested GDE.

Figure 5A:
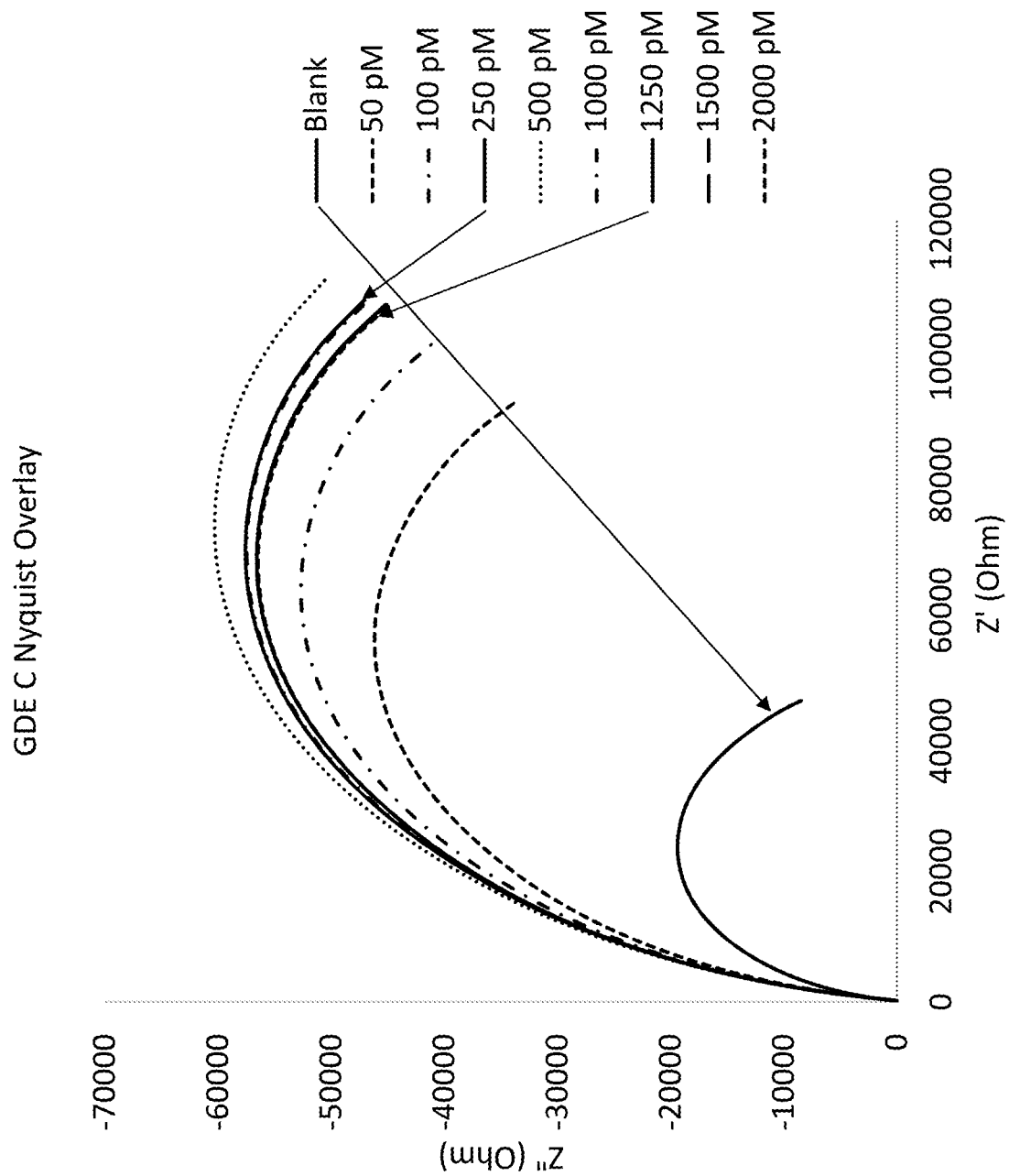
FIGS. 5A-5C show the validation of GDE C to measure insulin.
Figure 5B:
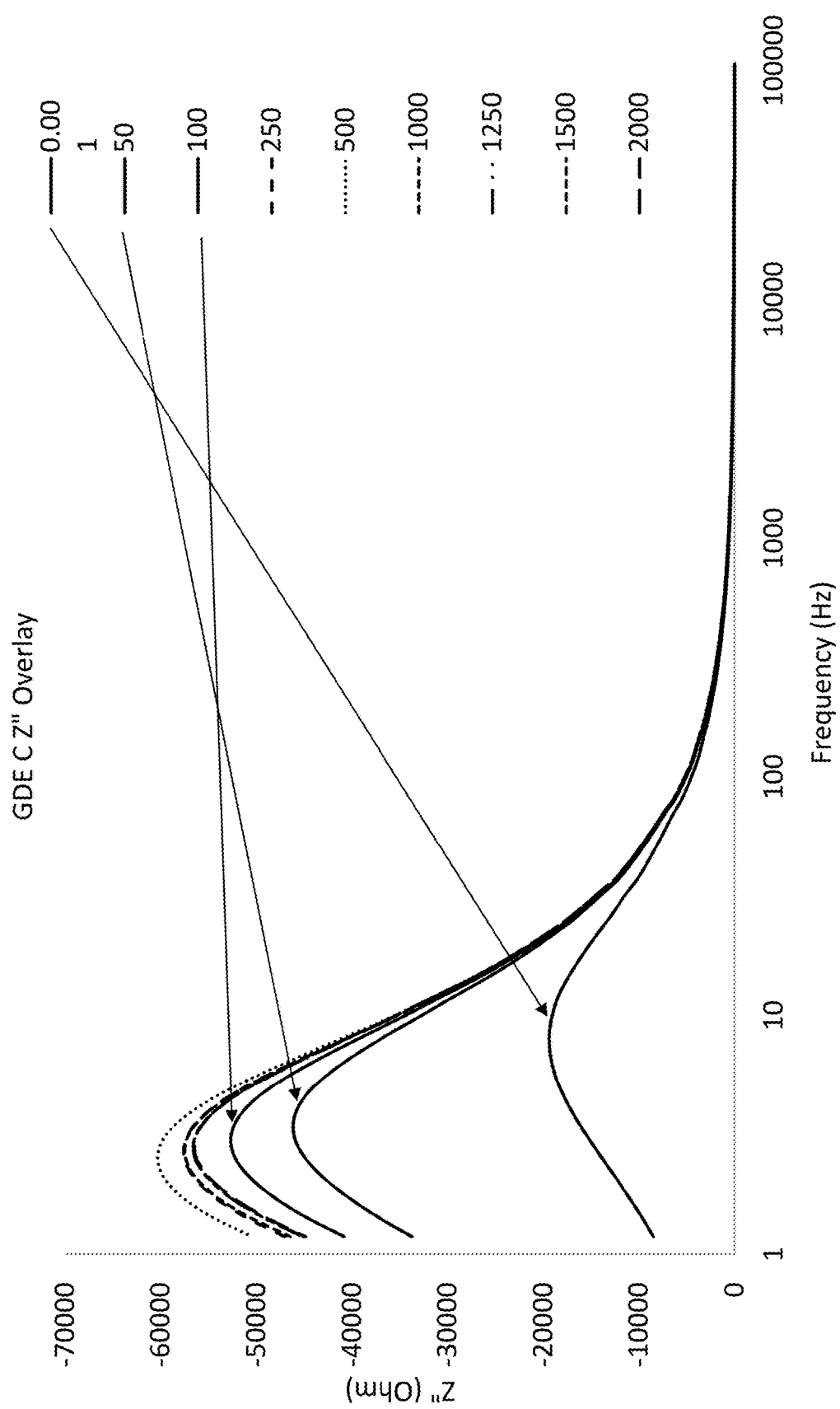
Figure 5C:
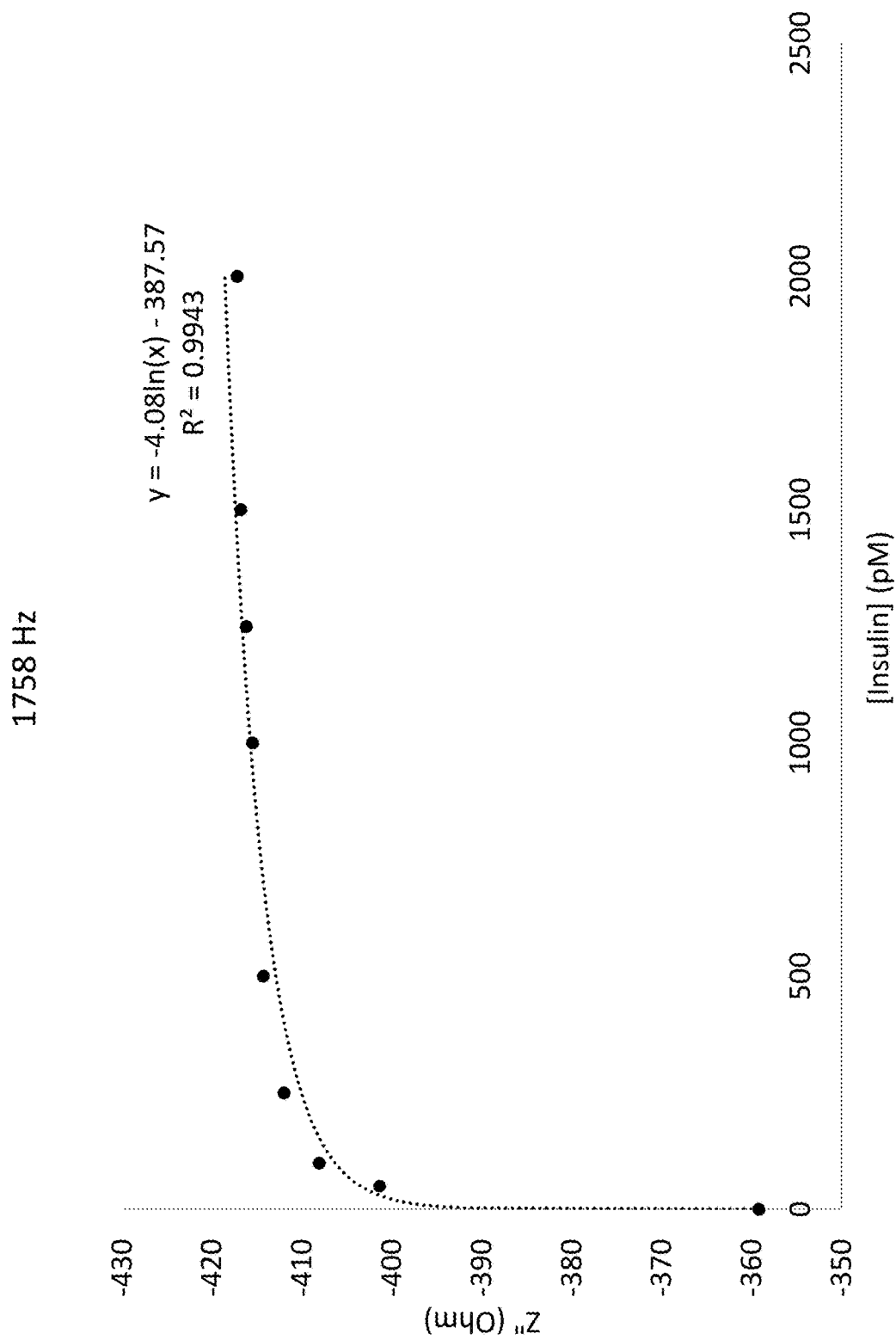
Figure 6A:
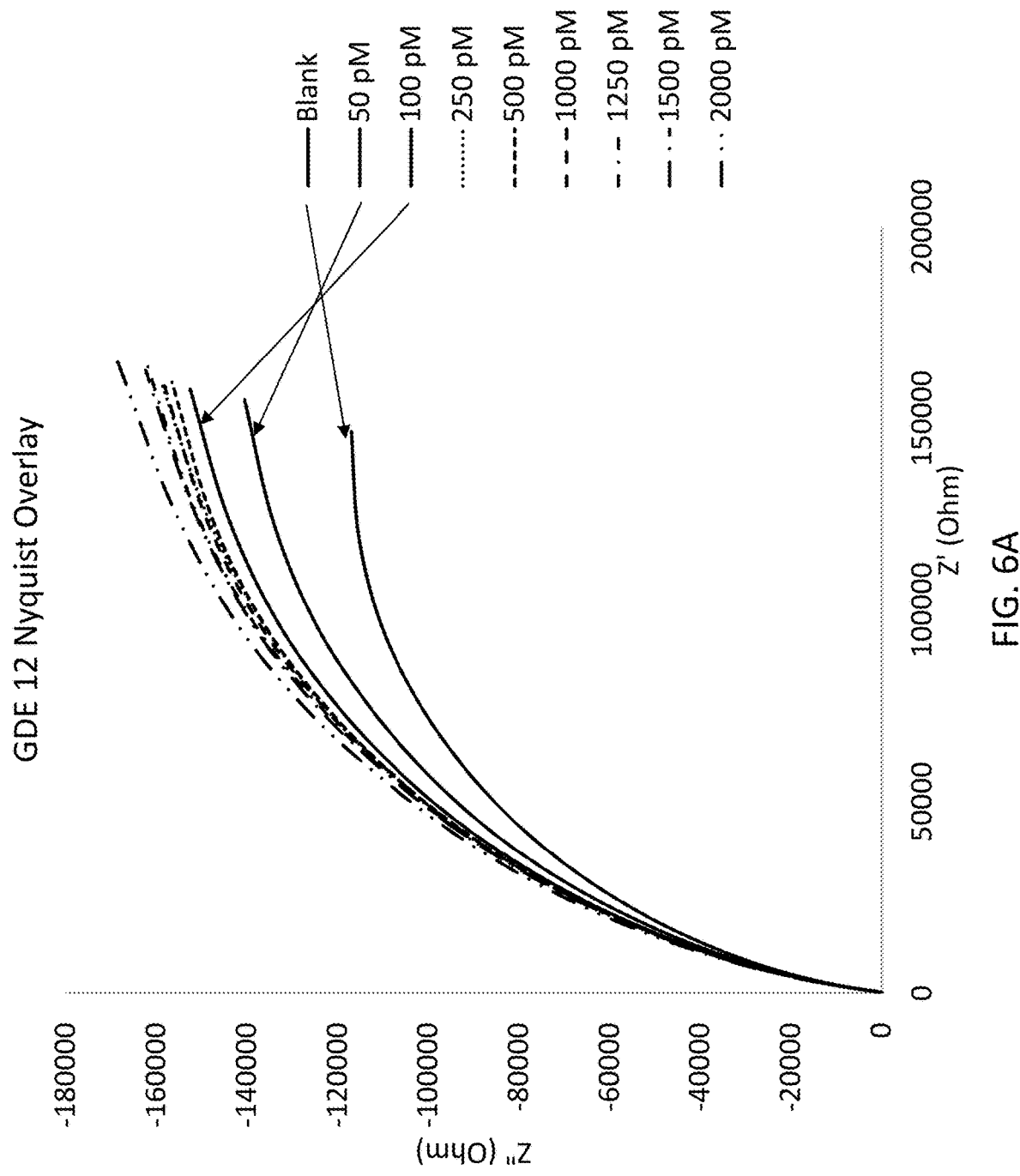
FIGS. 6A-6C show the validation of CDE 12 to measure insulin.
Figure 6B:
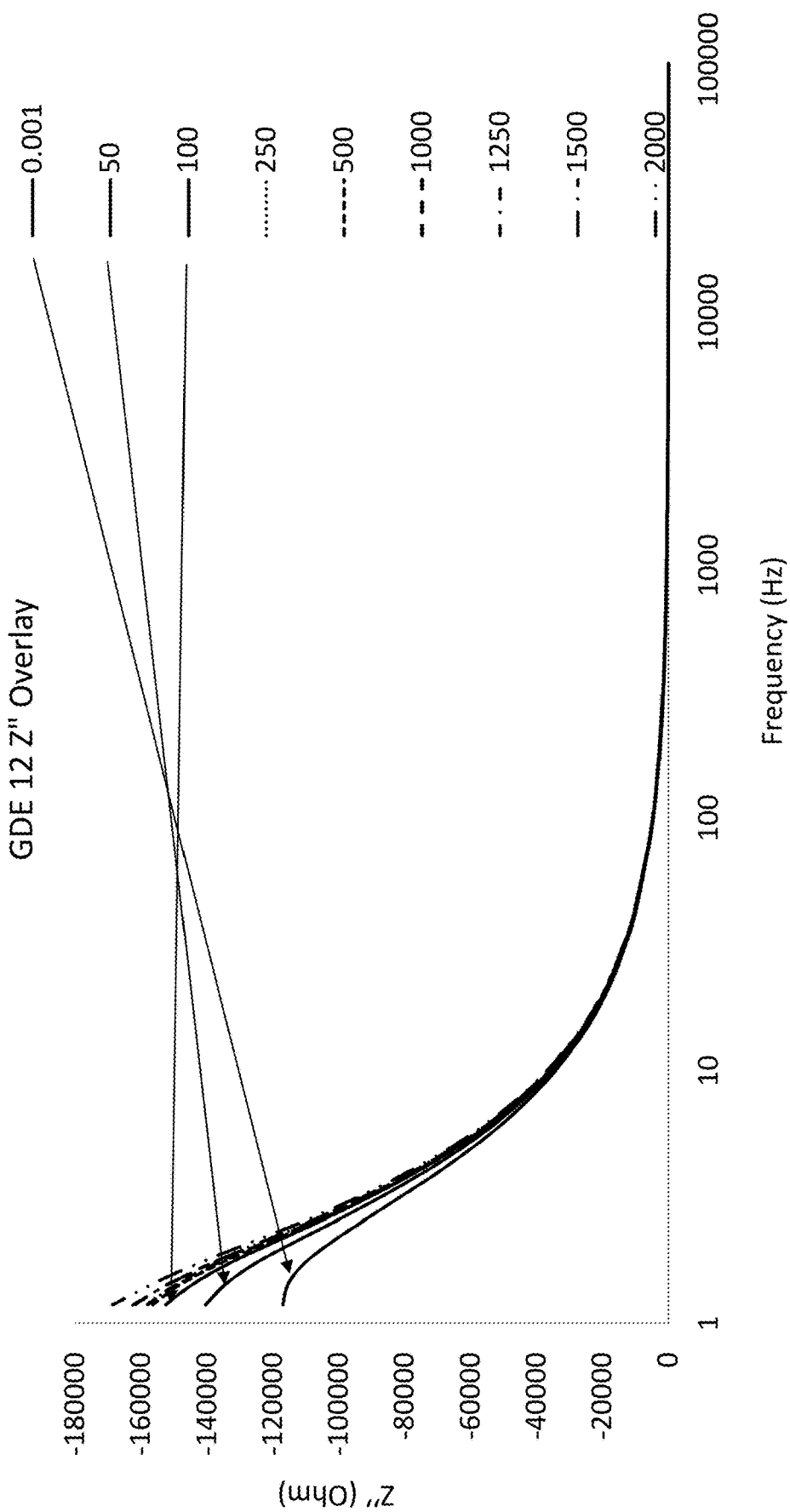
Figure 6C:
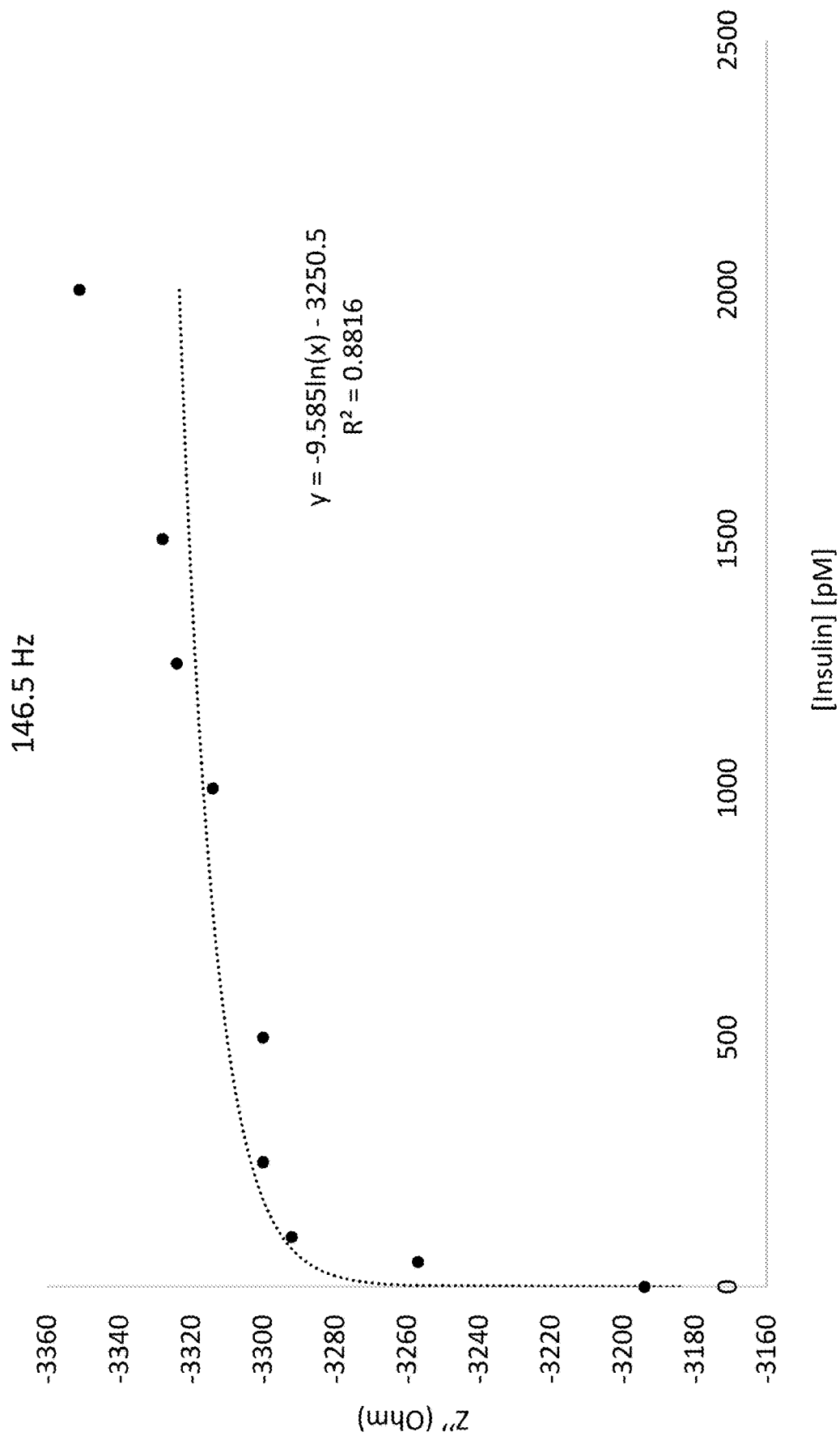

Starting from low insulin concentration to a high insulin concentration, AC Impedance was performed for all GDEs. Part of the working electrode was uncoated. Once the lowest concentration was tested for each GDE, the insulin concentration was increased and each GDE was re-tested until the insulin gradient was complete. The experiments were performed for 200 min. Results are shown in FIGS. 5A-5C (1758 Hz) and 6A-6C (146.5 Hz).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses, as well as the following claims:

Clause 1. A biosensor array for detecting an analyte in a subject, the biosensor array comprising: a plurality of sensor cells comprising at least one electrode; at least one antibody immobilized on a surface of the at least one electrode; and a biodegradable coating in direct contact with the at least one antibody.

Clause 2. The biosensor array of clause 1, wherein the analyte is insulin.

Clause 3. The biosensor array of clause 1 or clause 2, wherein the at least one antibody binds to insulin.

Clause 4. The biosensor array of any of clauses 1-3, wherein the biodegradable coating comprises one or more of polyglycolic acid, polylactic acid, or co-polymers thereof.

Clause 5. The biosensor array of any of clauses 1-4, wherein the plurality of sensor cells contain the biodegradable coating, and wherein the biodegradable coating comprises varying degrees of thickness.

Clause 6. The biosensor array of any of clauses 1-5, wherein the at least one electrode is a working electrode, wherein the biosensor array further comprises a counter electrode and a reference electrode, and wherein the at least one antibody is immobilized on a surface of the working electrode.

Clause 7. The biosensor array of any of clauses 1-6, wherein the biosensor array comprises at least 72 sensor cells.

Clause 8. The biosensor array of any of clauses 1-7, wherein the biosensor array comprises 96 sensor cells.

Clause 9. The biosensor array of any of clauses 1-8, wherein the biosensor array is about 0.1 mm-10 mm thick.

Clause 10. The biosensor array of any of clauses 1-9, wherein the biosensor array is about 0.1 mm-5 mm thick.

Clause 11. The biosensor array of any of clauses 1-10, wherein the biosensor array is implanted in the subject.

Clause 12. The biosensor array of any of clauses 1-11, wherein the subject is human.

Clause 13. A method for detecting an analyte in a subject, the method comprising: implanting the biosensor array of any one of clauses 1-12 in the subject; and detecting an analyte in the subject.

What is claimed is:

1. An implantable biosensor for detecting insulin comprising:
   an implantable biosensor array comprising a plurality of sensor cells comprising at least one working electrode, a counter electrode, and a reference electrode;
   one or more insulin-specific antibodies immobilized on a surface of the at least one working electrode;
   each sensor cell containing a biodegradable gelatin coating of varying thicknesses in direct contact with the one or more insulin-specific antibodies; and
   where upon subcutaneous implantation in a subject, the various thicknesses of biodegradable gelatin coating degrade at different rates over a period of 1 week to 6 months thereby exposing the insulin-specific antibodies at varying time points.

2. The biosensor of claim 1, wherein the biosensor array comprises at least 72 sensor cells.

3. The biosensor of claim 1, wherein the biosensor array comprises 96 sensor cells.

4. The biosensor of claim 1, wherein the biosensor array is about 0.1 mm-10 mm thick.

5. The biosensor of claim 1, wherein the biosensor array is about 0.1 mm-5 mm thick.

6. A method for detecting insulin, the method comprising:
   subcutaneously implanting the biosensor of claim 1 in a subject;

after the biodegradable gelatin coating degrades over the period of 1 week to 6 months exposing the insulin-specificantibody site, detecting insulin in the subject.

* * * * *